United States Patent [19]

Shalaby et al.

[11] 4,140,678
[45] Feb. 20, 1979

[54] SYNTHETIC ABSORBABLE SURGICAL DEVICES OF POLY(ALKYLENE OXALATES)

[75] Inventors: Shalaby W. Shalaby, Long Valley; Dennis D. Damiolkowski, Paterson, both of N.J.

[73] Assignee: Ethicon, Inc., Somerville, N.J.

[21] Appl. No.: 806,048

[22] Filed: Jun. 13, 1977

[51] Int. Cl.$^2$ ............................................. C08G 63/12
[52] U.S. Cl. ............................................ 260/860; 3/1; 128/335.5; 206/63.3; 528/272
[58] Field of Search ................... 260/75 R; 128/335.5

[56] References Cited

U.S. PATENT DOCUMENTS

| | | | |
|---|---|---|---|
| 2,111,762 | 3/1938 | Ellis | 260/75 R X |
| 2,952,652 | 9/1960 | Beindorff et al. | 260/75 R X |
| 4,032,993 | 7/1977 | Coguard et al. | 260/75 R X |

OTHER PUBLICATIONS

Carothers, W. H. et al., Journ. Amer. Chem. Soc., 52, pp. 3292–3300, (1930).
Savinov, V. M. et al., Polymer Science USSR, 6, pp. 1475–1481, (1964).

*Primary Examiner*—Lucille M. Phynes
*Attorney, Agent, or Firm*—Wayne R. Eberhardt

[57] ABSTRACT

Synthetic filaments composed of homopolymers and copolymers of poly(alkylene oxalates) are absorbable in animal tissue with minimal adverse tissue reaction. Polymers prepared by reacting a dialkyl oxalate with an alkylene diol are melt spun and drawn to obtain oriented fibers having good tensile properties and a high level of flexibility and softness. The filaments are particularly useful in the preparation of surgical prosthesis comprising woven or knitted fabrics and meshes. Other absorbable surgical devices including films and molded items may also be prepared from the disclosed polymer.

11 Claims, No Drawings

SYNTHETIC ABSORBABLE SURGICAL DEVICES OF POLY(ALKYLENE OXALATES)

BACKGROUND OF THE INVENTION

1. Field of the Invention

This invention relates to synthetic absorbable devices, and more particularly, to synthetic absorbable filaments comprising extruded and oriented polymers of poly(alkylene oxalates).

2. Description of Prior Art

Absorbable filamentary materials have traditionally been comprised of natural collagenous materials obtained from sheep or beef intestine, commonly known as catgut. More recently, it has been proposed to manufacture synthetic absorbable fibers from polyesters of hydroxycarboxylic acids, notably polylactide, polyglycolide, and copolymers of lactide and glycolide. Such synthetic absorbable products are described in U.S. Pat. Nos. 3,636,956, 3,297,033, and elsewhere in the literature. Polyesters of succinic acid have also been suggested for at least partially bioresorbable surgical articles as disclosed, for example, in U.S. Pat. No. 3,883,901.

The present invention provides for polymers of poly(alkylene oxalate) to be melt extruded into pliable, monofilament fibers having a high level of softness and flexibility and which are absorbable in animal tissue without significant adverse tissue reaction. The fibers have good initial tensile and knot strength and can be sterilized with cobalt-60 without serious loss of these properties. The higher alkylene oxalate polymes have good in vivo strength retention and are absorbed slowly while the lower alkylene oxalate polymers are characterized by rapid absorption.

Polymers of poly(alkylene oxalates) and the preparation thereof are described in the art. Carothers et al, J. Amer. Chem.. Soc. 52, 3292(1930), for example, describes the ester interchange reaction of diols such as ethylene glycol, 1,3-propanediol, or 1,4-butanediol with diethyl oxalate to yield a mixture of monomer, soluble polymer and insoluble polymer. The reaction of oxalic acid and an alkylene glycol to form polyester resins is described in U.S. Pat. No. 2,111,762, while the preparation of polyesters of fiber-forming quality from dicarboxylic acids and diols is described in U.S. Pat. No. 2,952,652. Superpolyesters of fiber-forming quality and derived from dibasic acids plus glycols are described in U.S. Pat. Nos. 2,071,250 and '251. Linear polyesters of oxalic acid have been reported as having high melting points, being soluble in many solvents, capable of forming films, and readily hydrolyzed [Savinov et al, Polymer Science USSR 6, 1475 (1964)].

The absorbability of poly(alkylene oxalate) polymers in animal tissue has not been known prior to the present invention, and there has been no suggestion in the art for the use of poly(alkylene oxalate) polymers in surgical applications. In particular, there has been no suggestion in the art that absorbable fibers having good tensile properties could be prepared from poly(alkylene oxalate) polymers or that such fibers would have any useful application in the fabrication of surgical devices.

It is accordingly an object of the present invention to provide new and useful articles of poly(alkylene oxalate) polymers. A further object of this invention is to provide synthetic absorbable filaments of poly(alkylene oxalate). It is yet a further object of this invention to provide absorbable surgical aids and prostheses fabricated of fibers or cast or machined from blocks of poly(alkylene oxalate) polymers.

SUMMARY

Synthetic absorbable filaments and other surgical aids are prepared from poly(alkylene oxalate) polymers having the formula:

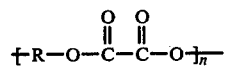

wherein R is $C_3$ to $C_{16}$ alkylene and n is the degree of polymerization resulting in a fiber-forming polymer having an inherent viscosity (as hereinafter defined) of at least about 0.4.

Polymers prepared by the transesterification reaction of an alkylene diol and diethyl oxalate are melt extruded into filaments suitable for use in the fabrication of surgical aids. The filaments are characterized by high tensile and knot strength with a high degree of softness and flexibility as characterized by a Young's modulus of less than about 600,000.

DESCRIPTION OF PREFERRED EMBODIMENTS

Polymers of the present invention are comrised of units having the general formula:

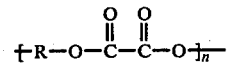

wherein R is a $C_3$ to $C_{16}$ alkylene, most preferably $C_4$ to $C_{10}$ alkylene, and n is the degree of poymerization resulting in a fiber-forming polymer and preferably in a polymer having an inherent viscosity of at least about 0.4 as determined at 25° C. on a 0.1 percent solution of polymer in chloroform or hexafluoroisopropanol (HFIP).

Alkylene oxalate polymers of the present invention are conveniently prepared by an ester interchange reaction between an lkylene diol and a lower ester of oxalic acid in the presence of an ester interchange catalyst. The diol is preferably a $C_3$ $C_{16}$ alkylene diol, and the ester of oxalic acid preferably diethyl oxalate. The ester interchange is preferably conducted in two stages wherein the reactants are first heated with stirring under a nitrogen atmosphere to form a prepolymer with the removal of ethanol, followed by postpolymerization under heat and reduced pressure to obtain a final polymer of the required molecular weight.

The polymer is melt extruded through a spinnerett in a conventional manner to form one or more filaments which are subsequently drawn about 4X to 6X in order to achieve molecular orientation and improve tensile properties. The resulting oriented filaments are characterized by a straight tensile strength of at least 30,000 psi and a crystallinity of at least about 15 percent.

To further improve dimensional stability and in vivo strength retention, the oriented filaments may be subjected to an annealing treatment. This optional annealing treatment consists of heating the filaments to a temperature of from about 40° to 80° C., most preferably from about 40° to 60° C. while restraining the filaments to prevent any substantial shrinkage. The filaments are held at the annealing temperature for a few seconds to several days or longer depending on the temperature and processing conditions. In general, annealing at 40° to 60° C. for up to about 24 hours is satisfactory for poly(alkylene oxalate). Optimum annealing time and temperature for maximum improvement in fiber in vivo strength retention and dimensional stability is readily determined by simple experimentation for each particular fiber composition.

The preparation of high molecular weight oriented filaments of poly(alkylene oxalate) is further illustrated by the following examples where all percentages are by weight unless otherwise noted. The following analytical methods were used to obtain the data reported in the examples. Inherent viscosity ($N_{inh}$) was determined at 25° C. on a 0.1 percent solution of polymer in chloroform or hexafluoriosopropanol (HFIP). The infrared spectra of polymer films (cast from $CHCl_3$ or HFIP) were recorded on a Beckman Acculab 1 spectrophotometer. The NMR spctra of the polymer solutions in $CDCl_3$ were recorded on an MH-100 or CFT-20 spctrometer. A DuPont 990 DSC apparatus was used to record the glass transition ($T_g$), crystallization ($T_c$) and melting temperatures ($T_m$) of the polymers in nitrogen, using 4 mg samples and a heating rate of 10° C./min or as otherwise specified. The thermogravimetric analysis (TGA) data of the polymers were recorded in nitrogen using a DuPont 950 TGA apparatus at a heating rate of 10° C./min and with 10 mg samples. A Philips vertical goniometer with graphite crystal monochromatized copper Kα-radiation was used to obtain the X-ray powder and fiber diffraction patterns of the polymers. Crystallinity was determined by the method of Hermans and Weidinger and the diffractometer patterns were resolved with a DuPont 310 curve analyzer.

In vitro hydrolyses of polymer discs (about 1.2 g, 2.2 cm diameter) and monofilaments (8-25 mil) were conducted in a phosphate buffer of pH 7.25 at 37° C.

In vivo absorption (muscle) was determined by implanting two 2 cm segments of monofilament fiber into the left gluteal muscles of female Long-Evans rats. The implant sites were recovered after periods of 60, 90, and 120 and 180 days and examined microscopically to determine the extent of absorption. In vivo absorption (subcutaneous) is a nonhistological technique in which continuous observation of the biological degradation of segmens of the filament were made by implanting two filaments, 2 cm long, into the abdominal subcutis of young female rats. The implants are readily visible when the skin is wetted with propylene glycol and extent of absorption can be determined by subjective visual examination.

In vivo strength retention was determined by implanting segments of filaments in the posterior dorsal subcutis of female Long-Evans rats for a period of 5 to 30 days. The samples were recovered at the designated periods and pull-tested for straight tensile strength.

EXAMPLES

General Polymerization Procedure

Diethyl oxalate was heated with a selected diol in a stirred reactor using a stannous alkanoate or oxalate or an organic titanate as a catalyst. The reaction was conducted uner a nitrogen atmosphere at suitable temperatures until a substantial portion of the calculated amont of ethanol was obtained. Postpolymerization of the resulting prepolymer was then continued under reduced pressure using a suitable heating scheme. At the end of the postpolymerization period, the molten polymer was allowed to cool slowly at room temperature, isolated, ground and redried at 25°;0 to 80° C. (depending on the polymer $T_m$) in vacuo for at least one day. Detailed experimental conditions for the preparation of representative samples of linear polyalkylene oxalates and important properties of the resulting polymers are presented below.

EXAMPLE 1

Poly(trimethylene oxalate)

Distilled 1,3-propanediol (17.48 g, 0.23 mole) and diethyl oxalate (29.2 g, 0.2 mole) were mixed with a catalytic amount of stannous oxalate (4.1 mg, 0.02 mmole) under nitrogen. The mixture was heated with stirring while allowing the resulting ethanol to distill at 150°, 120° and 150° C. for 0.5, 2 and 4 hours, respectively. The resulting polymer was then cooled to about 100° C. and the pressure was reduced to 0.1 mm. The polymerization was continued in vacuo at 150°, 160°, 180° and 200° C. for 1, 3, 1 and 2 hours, respectively. The polymeric product was recovered as a clear, soft material.

Polymer Characterization $N_{inh}$ in $CHCl_3$ = 0.57;
DSC (20° C./min): $T_g$ = −1° C.

EXAMPLE 2

Poly(tetramethylene oxalate)

Diethyl oxalate (36.5 g, 0.25 mole) was mixed with 1,4-butanediol (45 g, 0.5 mole) and a 1 percent solution of tetrakis( 2-ethylhexyl) titanate (TOT) catalyst (1 ml, 0.012 mmole) and transferred to a resin kettle under a dry nitrogen atmosphere. A prepolymer was formed by heating the reaction mixture under a nitrogen atmosphere for 2 hours each at 140° and 160° C. while allowing the formed ethanol to distill. The mixture was then heated under reduced pressure (2-3 mm Hg) at 160° and 180° C. for 20 and 2 hours, respectively. The polymer melt was slow-cooled, quenched in liquid nitrogen, isolated and ground. The ground polymer was redried at room temperature, in vacuo.

Polymer Characterization $N_{inh}$ in HFIP = 0.95
DSC (20° C./min): $T_g$ = 4.5; $T_c$ = 22; $T_m$ = 105° C.

Polymer Melt-Spinning and Fiber Properties

The polymer was spun using an Instron Rheometer at 110° C. with a 30 mil die and a shear rate of 841 $sec^{-1}$. The extrudates were quenched in ice water, wound and dried in vacuo at 25° C. The fibers were drawn 5X at 32° C. and the properties of the drawn fibers were as follows:

Inherent viscosity in HFIP: 0.79
DSC data (10° C./min): $T_g$ = 15; $T_m$ = 103° C.
X-ray data: 50% crystallinity
Physical properties:
Fiber diameter = 12.9 mil
Straight tensile strength = 34,500 psi
Elongation = 39%
Modulus = 2.19 + $10^5$ psi In vivo properties: After 5 days of implantation in rat muscle, the initial tensile strength of the fiber was reduced from 4.0 lbs to zero. Subcutaneous implantation of the fibers in rats indicates that 50 percent of their apparent mass was absorbed in the first 9 days, and 10 percent remained after 15 days, and absorption was substantially complete after 28 days.

In vitro hydrolysis data: Drawn fibers lost 67 percent of their initial mass in 7 days.

EXAMPLE 3

Poly(hexamethylene oxalate)

Distilled diethyl oxalate (73.1 g, 0.500 mole) was mixed with 1,6-hexanediol (61.2 g, 0.519 mole) and stannous octoate catalyst (0.33 M in toluene; 0.3 ml, 0.1 mmole) under a dry nitrogen atmosphere in a glass reactor equipped with a mechanical stirrer. A prepolymer was formed by heating the mixture at 120° C. for 2 hours and then at 160° C. for 3 hours under nitrogen at 1 atmosphere while allowing the formed ethanol to distill. The prepolymer was then heated for one hour in vacuo (0.1 mm Hg) at 80° and then 90° C. the post-polymerization of the polymer melt was completed by heating at 100°, 115°, 135°, 150°, 170°, 190° and 200° C. for 2, 1, 1.5, 4, 6, 1 and 6.5 hours, respectively. The polymer was allowed to cool at room temperature, quenched in liquid nitrogen, isolated and ground. The ground polymer was dried in vacuo at room temperature.

Polymer Characterization $N_{inh}$ in $CHCl_3$ = 0.83
DSC (10° C./min): $T_m$ = 70° C.

Polymer Melt-Spinning and Fiber Properties

The polymer was spun using an Instron Rheometer at 105° C. with a 40 mil die. The extrudates were quenched in ice water, wound and dried in vacuo. The fibers were drawn 5X at room temperaure and the properties of the drawn fibers were as follows:
X-ray date: 47% crystallinity
Physical properties:
Fiber diameter = 8.7 mils
Straight tensile strength = 5.22 × 10⁴ psi
Knot strength = 3.70 × 10⁴ psi
Elongation = 33%
Modulus = 1.89 × 10⁵ psi In vivo evaluation: After 3 days of implantation in the rat muscle, drawn fibers retained 35 percent of their original strength. No measurable strength was recorded after 7 days of implantation. After 42 days, absorption of the fiber was about 20 percent complete and after 121 days absorption was substantially complete.

In vitro hydrolysis data: Drawn fibers lost 83 percent of their initial mass in 31 days.

EXAMPLE 4

Poly (octamethylene oxalate)

Using a similar system to that of Example 3, distilled diethyl oxalate (109.6 g, 0.750 mole), distilled 1,8-octanediol (113.6 g, 0.777 mole) and stannous octoate catalyst (0.33 M in toluene - 0.455 ml, 0.150 mmole) were mixed under a dry nitrogen atmosphere in a glass reactor equipped with a mechanical stirrer. A prepolymer was formed by heating the mixture at 120° C. for 12 hours under nitrogen while allowing the formed ethanol to distill. Prior to postpolymerization, the product was heated for 1 hour at 90° C. and 0.1 mm Hg. The postpolymerization of the stirred polymer melt was completed by heating at 110°, 135°, 150°, 170° and 200° C. for 3.5, 2.5, 4.5, 0.5 and 5 hours, respectively at 0.1 mm Hg. The polymer was cooled, quenched in liquid nitrogen, isolated, ground and dried in vacuo at room temperature. The polymer was then heated at 60° C. in vacuo for one hour and finally at 200° C. for 6 hours to yield the final product.

Polymer Characterization $N_{inh}$ in $CHCl_3$ = 0.88
DSC (10° C./min): $T_m$ = 75° C.

Polymer Melt-Spinning and Fiber Properties

The polymer was spun according to the procedure described in Example 3. The extrudates were quenched in an ice water bath and subsequently drawn 6X at 64° C. The properties of the drawn fibers were as follows:
Inherent viscosity in $CHCl_3$: 0.8
X-ray data: 54% crystallinity
Physical properties:
Fiber diameter = 8.8 mil
Straight tensile strength = 4.99 × 10⁴ psi
Knot tensile strength = 3.95 × 10⁴ psi
Elongation = 32%
Modulus = 1.81 × 10⁵ psi
DSC (10° C./min): $T_m$ = 75° C.

In vitro hydrolysis data: The drawn monofilaments lost, 15, 66 and 96 percent of their original weight after 18, 122 and 199 days respectively.

In vivo evaluation: Drawn monofilaments implanted in the posterior dorsal subcutis retained 79, 19 and 0 percent of their original breaking strength (3.16 lbs) after 3, 7 and 14 days, respectively. Fibers implanted into the gluteal muscles of rats to determine their absorption and tissue response characteristics at 3, 21, 42 and 119 days postimplantation showed no absorption up to the 42-day period. At the 119-day period, there was evidence of minimal absorption of some of the fibers.

EXAMPLE 5

Poly(decamethylene oxalate)

1,10-Decanediol (87.1 g, 0.5 mole) was mixed with diethyl oxalate (58.4 g, 0.4 mole) and a solution of TOT catalyst in toluene (0.012 mmole) under a nitrogen atmosphere. The reaction mixture was heated with stirring while allowing the resulting ethanol to distill at 120°, 130° and 140° C for 4, 2.5 and 2 hours respectively. The pressure was then reduced to 0.5 mm while heating to 190° C. for 20 minutes. The polymerization was continued in vacuo at 190° and 210° C. for 4 and 13 hours, respectively. The polymer was recovered and characterized as follows:

Polymer Characterization $N_{inh}$ in $CHCl_3$ = 0.45
DSC (10° C./min): $T_m$ = 77.5° C.

Polymer Extrusion and Fiber Properties

The polymer was extruded at 84° C. using a 40 mil die. The resulting undrawn monofilament had an average diameter of 19 mil.

In vitro hydrolysis data:
The undrawn monofilaments had a weight loss of 1, 11, 38 and 62 percent after 6, 17, 44 and 177 days, respectively.

EXAMPLE 6

Poly(dodecamethylene oxalate)

Distilled diethyl oxalate (14.6 g, 0.100 mole) was mixed with 1,12-dodecanediol (20.8 g, 0.103 mole) and stannous octoate catalyst (0.33 M in toluene — 0.061 ml, 0.02 mmole) under a dry nitrogen atmosphere in a glass reactor equipped for magnetic stirring. The prepolymer was formed after heating the mixture at 120° C. for 3 hours and 160° C. for 2 hours under nitrogen at 1 atmosphere while allowing the formed ethanol to distill. The mixture was then heated for 6 hours in vacuo (0.1 mm Hg) at 200° C. and then 210° C. for 2 hours. The postpolymerization of the polymer melt was completed after heating at 200° C. for 5 additional hours. The polymer was cooled at room temperature and recovered.

Polymer Characterization $N_{inh}$ in $CHCl_3$ = 0.57
DSC (20° C./min): $T_m$ = 91° C.

EXAMPLE 7

Poly(hexadecamethylene oxalate)

Using a similar system to that used for Example 6, diethyl oxalate (8.0 g, 0.055 mole), 1,16-hexadecanediol (14.6 g, 0.057 mole) and stannous octoate catalyst (0.33 M in toluene — 0.033 ml, 0.01 mmole) were mixed under an atmosphere of dry nitrogen in a glass reactor equipped for magnetic stirring. The prepolymer was formed after heating the mixture at 120° C. for 3 hours and then at 160° C. for 2 hours under nitrogen at 1 atmosphere while allowing the formed ethanol to distill. The mixture was then heated in vacuo at 0.1 mm Hg and at 200°, 210° and 230° C. for 2, 2 and 3 hours, respectively. The postpolymerization of the stirred polymer melt was completed after heating at 200° C. for 4 additional hours. The polymer was cooled and recovered.

Polymer Characterization $N_{inh}$ in $CHCl_3$ = 0.45
DSC (20° C./min): $T_m$ = 95° C., $T_g$ = 40° C.

While the preceding examples have been directed to the preparation of specific homopolymers of poly(alkylene oxalates), these examples are for purposes of illustration only and are not limiting of the invention. Copolymers of $C_3$ to $C_{16}$ alkylene oxalate with up to about 50 percent by weight of one or more other compatible monomers which produce nontoxic and absorbable polymers, and physical mixtures of homopolymers and copolymers, are likewise included within the present invention.

It is to be understood that inert additives such as coloring materials and plasticizers can be incorporated in the polymers of the present invention. Any of a variety of plasticizers such as, for instance, glyceryl triacetate, ethyl benzoate, diethyl phthalate, dibutyl phthalate and bis-2-methoxyethyl phthalate can be used if desired. The amount of plasticizer may vary from 1 to about 20 percent or more based on the weight of the polymer. Not only does the plasticizer render the filaments even more pliable, but it also serves as a processing aid in extrusion and thread preparation. As used herein, the term "inert" means materials that are chemically inert to the polymer, and biologically inert to living tissue, i.e., do not cause any of the adverse effects previously discussed.

Filaments of the present invention are adversely affected by moisture and are accordingly preferably packaged dry in a substantially moisture-free environment within a hermetically sealed package. A suitable package is fabricated of two sheets of aluminum foil or an aluminum foil-plastic laminate heat sealed or bonded with adhesive around the border of package to hermetically seal the cavity and isolate the contents of the package from the external atmosphere. The package may be evacuated or filled with a dry, inert gas such as air or nitrogen. Such packages are conventionally used for storing hydrolytically sensitive materials comprised of polymers of glycolide and/or lactide as illustrated, for example, in U.S. Pat. No. 3,636,956.

Filaments of the present invention may be used as monofilaments or multifilaments and may be woven, braided, or knitted alone or in combination with other absorbable fibers such as polyglycolide or poly(lactide-co-glycolide), or in combination with nonabsorbable fibers such as nylon, polypropylene, polyethyleneterephthalate, or polytetrafluoroethylene to form surgical fabrics and tubular structures having use in the repair of arteries, veins, ducts, esophagi and the like. Those filaments which have an initial straight tensile strength and knot strength of at least 40,000 psi and 30,000 psi respectively, retain a substantial portion of their initial tensile strength after 21 days in vivo, and are substantially completely absorbed in vivo within about 6 months, are also useful as synthetic absorbable sutures.

Multifilament yarns constructed of the poly(alkylene oxalate) filaments of the present invention together with nonabsorbable filaments are useful in the fabrication of surgical fabrics which are only partially absorbable for applications where long-term fabric strength retention is desirable even after the absorbable components have been replaced by natural tissue growth into the fabric. The relative proportions of absorbable filaments and nonabsorbable filaments may be varied to obtain the absorption and strength retention characteristics desired in the particular fabric or tubular implant.

Composite fabrics of absorbable and nonabsorbable materials may be fabricated by conventional textile processes such as weaving, knitting and nonwoven felting as described in U.S. Pat. Nos. 3,108,357 and 3,463,158. Methods of weaving and crimping tubular vascular prostheses are described in U.S. Pat. No. 3,096,560. In addition, surgical aids may be composed of "bi-component filaments" of absorbable and nonabsorbable components as described in U.S. Pat. No. 3,463,158, the teaching of which is incorporated herein by reference.

Fabrics containing filaments of the present invention are useful in surgical applications where an absorbable aid or support is required, as for example, in hernia repair and in supporting damaged liver, kidney and other internal organs where a temporary aid during healing is needed.

The polymers of the present invention are also useful in the manufacture of cast films and other solid surgical aids such as scleral buckling prostheses. Thus, absorbable cylindrical pins, screws, reinforcing plates, and the like may be machined from the cast polymer.

Many additional embodiments of this invention will be apparent to those skilled in the art and may be made without departing from the spirit and scope thereof. It is accordingly understood that this invention is not limited to the specific embodiments thereof except as defined in the appended claims.

What is claimed is:

1. A sterile absorbable surgical fiber comprising a polymer having a major portion of units of the formula

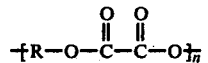

wherein R is a $C_3$ to $C_{16}$ alkylene and n is the degree of polymerization resulting in a fiber-forming polymer having an inherent viscosity of at least about 0.4 as determined at 25° C. on a 0.1 percent solution of polymer in chloroform or hexafluoroisopropanol.

2. A fiber of claim 1 further characterized by a straight tensile strength of at least 30,000 psi and a Young's modulus of less than about 600,000 psi.

3. A fiber of claim 2 wherein R is a $C_4$ to $C_{10}$ alkylene.

4. A fiber of claim 1 wherein said polymer is a copolymer of $C_3$ to $C_{16}$ alkylene oxalate with up to about 50 percent by weight of at least one other monomer copolymerizable therewith to form an absorbable polymer.

5. A fiber of claim 4 wherein said other monomer is lactide, glycolide or mixtures thereof.

6. A fiber of claim 1 comprising poly(tetramethylene oxalate).

7. A fiber of claim 1 comprising poly(hexamethylene oxalate).

8. A fiber of claim 1 comprising poly(octamethylene oxalate).

9. A fiber of claim 1 comprising poly(decamethylene oxalate).

10. A fiber of claim 1 comprising a major proportion of said polymer and a minor proportion of at least one other synthetic absorbable polymer.

11. A fiber of claim 10 wherein said other synthetic absorbable polymer is selected from the group consisting of homopolymers and copolymers of lactide and glycolide.

* * * * *

UNITED STATES PATENT AND TRADEMARK OFFICE
CERTIFICATE OF CORRECTION

PATENT NO. : 4,140,678
DATED : February 20, 1979
INVENTOR(S) : Shalaby W. Shalaby et al.

It is certified that error appears in the above-identified patent and that said Letters Patent are hereby corrected as shown below:

On the title page under Inventors: "Dennis D. Damiolkowski" should read -- Dennis D. Jamiolkowski --.

At Column 1, line 32: "polymes" should read -- polymers --.

At Column 2, line 27: "comrised" should read -- comprised --.

At Column 2, line 34: "poymerization" should read -- polymerization --.

At Column 2, line 43: "lkylene" should read -- alkylene --.

At Column 2, line 45: "$C_3C_{16}$" should read -- $C_3$ to $C_{16}$ --.

At Column 3, line 15: "hexafluoriosopropanol" should read -- hexafluoroisopropanol --.

At Column 3, line 18: "spctra" should read -- spectra --.

At Column 3, line 20: "spctrometer" should read -- spectrometer --.

At Column 3, line 45: "segmens" should read -- segments --.

At Column 3, line 62: "uner" should read -- under --.

UNITED STATES PATENT AND TRADEMARK OFFICE
CERTIFICATE OF CORRECTION

PATENT NO. : 4,140,678
DATED : February 20, 1979
INVENTOR(S) : Shalaby W. Shalaby et al.

It is certified that error appears in the above-identified patent and that said Letters Patent are hereby corrected as shown below:

At Column 4, line 1: "25° ;0 to 80°C" should read -- 25° to 80°C --.

At Column 4, line 63: "Modulus = 2.19 + $10^5$ psi" should read -- Modulus = 2.19 x $10^5$ psi --.

At Column 4, line 67: "indicates" should read -- indicated --.

At Column 5, line 36: "X-ray date" should read -- X-ray data --.

Signed and Sealed this

Eighteenth Day of March 1980

[SEAL]

Attest:

SIDNEY A. DIAMOND

Attesting Officer

Commissioner of Patents and Trademarks